(12) United States Patent
Brothers et al.

(10) Patent No.: US 7,112,314 B2
(45) Date of Patent: Sep. 26, 2006

(54) POLYMERIZATION EMPLOYING DIACYL PEROXIDE MADE IN APROTIC SOLVENT

(75) Inventors: Paul Douglas Brothers, Chadds Ford, PA (US); Brian Edward Kipp, Wilmington, DE (US); Charles Joseph Noelke, Wilmington, DE (US); Ronald Earl Uschold, West Chester, PA (US); Robert Clayton Wheland, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 0 days.

(21) Appl. No.: 10/846,793

(22) Filed: May 14, 2004

(65) Prior Publication Data

US 2004/0213723 A1   Oct. 28, 2004

Related U.S. Application Data

(62) Division of application No. 09/850,546, filed on May 7, 2001, now abandoned.

(60) Provisional application No. 60/207,005, filed on May 25, 2000.

(51) Int. Cl.
*C11D 1/00* (2006.01)
*C01B 15/16* (2006.01)

(52) U.S. Cl. .................................................. 423/305

(58) Field of Classification Search ................ 570/101, 570/123, 138, 140, 216, 237, 257
See application file for complete search history.

(56) References Cited

U.S. PATENT DOCUMENTS 2,792,423 A   5/1957   Young et al.
3,502,701 A *  3/1970  Lewis et al.
3,860,568 A *  1/1975  Chabert et al. ............. 526/117
3,936,506 A *  2/1976  Berthold
4,803,228 A *  2/1989  Jacquet et al.
5,021,516 A    6/1991  Wheland
5,820,841 A   10/1998  Chen et al.

FOREIGN PATENT DOCUMENTS

JP           81-152653           7/1986

OTHER PUBLICATIONS

Detar et. al, Journal of American Chemical Sociaty, (1955), vol. 77, issue 23, pp. 6370-6371.*
CA:50:48596 abs of J Am Chem Soc by De Tar et al 77 pp. 6370-6371 1955.*
Beilstein Reg No. 1773938 ab of J Amer Chem Soc by Kharasch et al 63 p. 527 1941.*
CA:67:32328 abs of NL 6604105 Dec. 1966.*
S. R. Sandler and W. Karo, (1974) Polymer Synthesis vol. 1, Academic Press, Inc., Orlando, Florida, p. 451.
A. McKillop and W. R. Sanderson, Tetrahedron, vol. 51, No. 22, pp. 6145-6168, 1995.
J. Muzart, Synthesis, pp. 1325-1346, Nov. 1995.
M. S. Cooper, et al. Synlett, pp. 533-535, Sep. 1990.
J. T. Kadia, et al., Polymer Preparation, vol. 39, No. 2, pp. 835-836, 1998.
D. F. Detar et al, J. Am. Chem. Soc., vol. 77, No. 23, 1955, pp. 6370-6371.
P. G. Webb et al., J. Am. Chem. Soc., vol. 93, No. 15, 1971, pp. 3730-3738.

* cited by examiner

*Primary Examiner*—Johann Richter
*Assistant Examiner*—Chukwuma Nwaonicha

(57) ABSTRACT

This invention relates to a process for the synthesis of diacyl peroxide by contacting acyl halide and peroxide complex in compatible aprotic solvent substantially free of compounds oxidizable by the peroxide complex or the reaction products of organic acyl halide with peroxide complex and the initiation of polymerization with diacyl peroxide in the aprotic solvent.

13 Claims, No Drawings

POLYMERIZATION EMPLOYING DIACYL PEROXIDE MADE IN APROTIC SOLVENT

FIELD OF THE INVENTION

This invention is in the field of the polymerization and more specifically is related to the synthesis of diacyl peroxide from acyl halide in compatible aprotic solvent and the use of diacyl peroxide in the aprotic solvent for the initiation of polymerization.

BACKGROUND OF THE INVENTION

Diacyl peroxides are among the commonly used initiators in the commercial production of polyolefins, particularly fluoroolefins, such as tetrafluoroethylene. They may be represented as R—(C=O)—O—O—(C=O)—R. The peroxide decomposes to give R., known as a free radical, which reacts with olefin monomer to begin the polymerization cycle. Taking tetrafluoroethylene as an example:

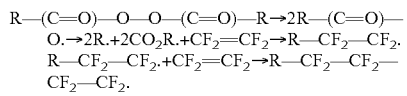

The R group arising from the initiator is called an "end-group" of the polymer.

The classical synthesis of diacyl peroxides is an aqueous synthesis. An alkaline aqueous solution of hydrogen peroxide is contacted with a water-immiscible solution of acid halide. Examples are found in S. R. Sandler and W. Karo, (1974) *Polymer Synthesis,* Vol. 1, Academic Press, Inc., Orlando Fla., p. 451 and U.S. Pat. No. 5,021,516. This is a reaction of two liquid phases, an aqueous phase and a nonaqueous phase. Equation (1) shows the reaction:

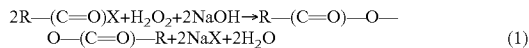 (1)

From the stoichiometry of (1) it is clear that one mole of hydrogen peroxide reacts with two moles of acyl halide to yield one mole of diacyl peroxide. The diacyl peroxide as it forms is taken up in the water immiscible phase. By this means, exposure of the acyl halide and the diacyl peroxide to the alkaline aqueous phase is minimized, which is desirable because water hydrolyzes both the organic acyl halide starting material and the diacyl peroxide product. Hydrolysis decreases yield and introduces byproducts such as acids and peracids, which are impurities. At the end of the reaction, the water-immiscible solvent with the diacyl peroxide dissolved in it is separated and dried, and purified as necessary.

The use of sodium percarbonate and sodium perborate for aqueous and nonaqueous functional group oxidation in organic synthesis has been reported (A. McKillop and W. R. Sanderson, *Tetrahedron,* vol. 51, no. 22, pp. 6145–6166, 1995; J. Muzart, *Synthesis* pp. 1325–1346, November 1995). Organic oxidation reactions using urea/hydrogen peroxide adduct in protic and aprotic solvents is reported by M. S. Cooper, et al. *Synlett,* pp. 533–535, September 1990. Organic acids, acid anhydrides, and acyl halides are reagents and solvents in these reactions and peracids are proposed as intermediates in the oxidations. Formation of diacyl peroxide as an undesirable byproduct of the reaction is discussed.

Japanese Patent 61152653 discloses the preparation of diacyl peroxides by the mixing of acyl halides with sodium peroxide ($Na_2O_2$) in halogenated solvent, followed by addition of water. Sodium peroxide must be handled carefully: it can react violently or explosively with organic materials, is hygroscopic, and absorbs carbon dioxide from air to form compounds that can ignite if subjected to pressure or friction. Furthermore, sodium peroxide, being strongly basic, cannot be used with compounds that are sensitive to bases.

A safe, economical, synthesis of diacyl peroxides in aprotic solvent using stable, easy to handle oxidizing agents, and proceeding in high yield is needed. Looking to the future, the need is greatest for a process that can be run in a nonflammable solvents such as fluorocarbons, chlorofluorocarbons, or certain hydrohalocarbons.

SUMMARY OF THE INVENTION

One form of this invention relates to a polymerization process for olefin monomer including the synthesis of diacyl peroxide by contacting organic acyl halide and peroxide complex, in compatible aprotic solvent substantially free of compounds oxidizable by the peroxide complex or by products of the reaction of organic acid halide with peroxide complex. Polymerization of olefin monomer is initiated with diacyl peroxide contained in the resulting solution. A second form of this invention relates to a polymerization process for olefin monomer including the continuous synthesis of diacyl peroxide by continuously contacting a feed stream comprised of organic acyl halide in a compatible aprotic solvent with a bed comprised of peroxide complex, to form a product stream comprised of diacyl peroxide in compatible aprotic solvent, the compatible aprotic solvent being substantially free of compounds oxidizable by peroxide complex or by products of the reaction of organic acid halide with peroxide complex. Polymerization of olefin monomer is initiated with diacyl peroxide contained in the resulting product stream.

DETAILED DESCRIPTION OF THE INVENTION

The present invention relates to a process for the synthesis of organic peroxides by contacting organic acyl halides with peroxide complexes in compatible aprotic solvents. Surprisingly, it has been found that diacyl peroxides can be prepared in good yield, and furthermore that yield improves when the peroxide complex is in molar excess relative to the acyl halide, which is contrary to expectations and to the teaching of the prior art, both of which would lead one to predict that diacyl peroxide yield would be depressed and peracid yield enhanced, by excess peroxide.

Organic acyl halides are compounds that can be represented by the structure R—(C=O)X. X represents halogen: fluorine, chlorine, bromine, or iodine. The most readily available acyl halides are generally acyl chloride or acyl fluoride. R represents any organic group that is compatible with one or more of the peroxide complexes useful for carrying out this invention under reaction conditions. A compatible R group is one that does not contain atoms or groups of atoms that are susceptible to oxidation by or otherwise react with the other ingredients in the course of the reaction or in the reaction mixture to give undesirable products. R groups acceptable in the present invention include aliphatic and alicyclic groups, these same groups with ether functionality, aryl groups and substituted aryl groups in which the substituents are compatible with one or more of the peroxide complexes of this invention under the conditions of the synthesis. The R group may be partially or completely halogenated. If perhalogenated, the R group may have only one type of halogen, as with perfluorinated groups, or may have several types, as with, for example, chlorofluorinated groups.

The R group may also contain certain functional groups or atoms such as —COOCH$_3$, —SO$_2$F, —CN, I, Br, or H. As stated above, the R group is incorporated in the polymer at the end of the polymer chain, that is, as an endgroup. It is sometimes useful to be able to further react the polymer through the endgroup with other molecules, for example, other monomers or polymer, or to introduce ionic functionality in the endgroup to promote interaction with polar surfaces such as metals, metal oxides, pigments, or with polar molecules, such as water or alcohols, to promote dispersion. Some of the functional groups above, for example —COOCH$_3$ and —SO$_2$F (the fluorosulfonyl group) are susceptible to hydrolysis, especially base-catalyzed hydrolysis, and reaction with nucleophiles. However, because of the absence of an aqueous phase in a preferred form of this invention and of the specificity of the peroxide complexes useful in carrying out this invention, these functional groups are not affected and the diacyl peroxides corresponding to these acyl halides can be made. The invention thereby provides novel acyl peroxide compounds having at least one fluorosulfonyl group in at least one of the acyl constituents. Preferably, at least one of the acyl constituents is derived from FSO$_2$CF$_2$(C=O)F. For example, from FSO$_2$CF$_2$(C=O)F, the novel compound FSO$_2$CF$_2$(C=O)—O—O—(C=O)CF$_2$SO$_2$F, bis[perfluoro(fluorosulfonyl)acetyl] peroxide, can be made without hydrolysis of the sulfonyl fluoride functionality to sulfonic acid. It is thus a further advantage of the processes according to this invention, that such hydrolysis-sensitive groups can be incorporated in diacyl peroxides and thereby introduced as endgroups in polymers.

In the synthesis of diacyl peroxide in accordance with this invention, no more than one organic acyl halide will normally be used. Although with more than one organic acyl halide the reaction would proceed satisfactorily, more than one diacyl peroxide would be made. For example, if two organic acyl halides are used, A—(C=O)X and B—(C=O)X, three diacyl peroxides would be expected: A—(C=O)—O—O—(C=O)—A, B—(C=O)—O—O—(C=O)—B, and A—(C=O)—O—O—(C=O)—B, a mixed diacyl peroxide. The ratio of the peroxides can be controlled to some extent by the order of addition of the organic diacyl halides. Such a mixture of peroxides is usually undesirable because different peroxides will generally have different decomposition rates. However, if a mixed diacyl peroxide is wanted, the method of this invention may be used, followed if necessary by separation or purification steps to reduce or remove accompanying unwanted peroxides.

Diacyl peroxides in which the acyl group is a hydrocarbon group can be made according to this invention. These hydrocarbon diacyl peroxides are useful for initiation of olefin polymerization, including fluoroolefin polymerization when the presence of a hydrocarbon endgroup is acceptable or desirable. Isobutyryl peroxide is preferred when a low temperature hydrocarbon initiator is needed. It can be made from isobutyryl halide, preferably isobutyryl chloride.

Synthesis of diacyl peroxides according to this invention is particularly useful for making initiators for the polymerization of fluoroolefins such as tetrafluoroethylene, hexafluoroproplyene, perfluoro(alkyl vinyl ethers), chlorotrifluoroethylene, vinylidene fluoride, and vinyl fluoride, either as homopolymers, or as copolymers with each other or with other olefins, such as ethylene and perfluoroalkylethylenes. Fluoroolefin polymerization is susceptible to chain transfer if compounds with labile carbon-hydrogen bonds are present, so it is desirable that initiators be free of such bonds. Furthermore, because of the high temperatures at which fluoropolymers are processed and the conditions under which they are often used, the thermal and hydrolytic stability of the polymer endgroups is important. The R group of the initiator is one source of such endgroups. Therefore, except in cases where specific reactivity of polymer endgroups is wanted, in the interest of minimizing chain transfer activity of the initiator and of providing endgroups with thermal and hydrolytic stability comparable to that of the polymer chain, it is desirable that the R group be free of bonds that are capable of chain transfer or that are less thermally or hydrolytically stable than the polymer itself. In polymerizing fluoromonomers, perhalogenated R groups, and preferably perfluorinated R groups, meet this requirement. Because ether functionality in halogenated and fluorinated organic groups has good thermal and oxidative stability if the oxygen is between carbon atoms that are perhalogenated or perfluorinated, or between carbon atoms that are substituted with perhaloalkyl or perfluoroalkyl groups, such ether functionality is acceptable also.

It is a further advantage of diacyl peroxide synthesis in accordance with this invention that fluoroorganic acyl halides, that is, acyl halides in which the R group is at least partially fluorinated, and particularly perfluoroorganic acyl halides, are readily reacted to form the corresponding diacyl peroxides. An example of a perfluoroorganic acyl halide for this invention is perfluoro(2-methyl-3-oxa-hexanoyl fluoride), also known as hexafluoropropylene oxide (HFPO) dimer acid fluoride and as DAF. It has the formula:

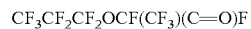

CF$_3$CF$_2$CF$_2$OCF(CF$_3$)(C=O)F

Other suitable perfluoroorganic acyl halides include CF$_3$CF$_2$CF$_2$(C=O)Cl (heptafluorobutyryl chloride) and CF$_3$CF$_2$(C=O)F (pentafluoropropionyl fluoride).

The peroxide complexes useful for carrying out this invention include a) complexes of hydrogen peroxide with inorganic compounds, referred to here as inorganic complexes, and b) complexes of hydrogen peroxide with organic molecules, referred to here as organic peroxide complexes. These include those substances in which hydrogen peroxide is combined with inorganic or organic compounds by bonds strong enough to permit isolation of the compounds, though the bonds may be weaker or of a different character than those between the constituents of hydrogen peroxide or of the compound with which it is complexed. By this criterion it can be seen that "sodium percarbonate", which is isolable and has the composition Na$_2$CO$_3$.1½H$_2$O$_2$, is a complex of hydrogen peroxide, while an aqueous solution of hydrogen peroxide, although it may have degrees of hydration that vary with concentration, is not. Complexes, as the term is used here, also include compounds such as sodium perborate, in which the elements of peroxide are reported to be an integral part of the molecule. The complexes according to this invention do not include persulfates or monopersulfates, such as potassium monopersulfate (KHSO$_5$), which are found to be ineffective. It is believed that the stability oxygen-sulfur bond in the persulfate is so great that persulfates cannot provide the elements of hydrogen peroxide needed for this synthesis. Apart from these stipulations, nothing is implied as to the structure of the complexes. They may be combinations of hydrogen peroxide with the inorganic compound or organic molecule in which the peroxide is associated through weak or strong bonds. Alternatively, they may be reaction products of peroxide with the compound or molecule, in which elements of the peroxide are incorporated in the structure of the compound or molecule, but are available for reaction with acid halides. For some complexes, the structures may be unknown. It is preferable that the complexes be dry. It is more preferable that the complexes be anhydrous. The term "dry" means essentially free of water, though waters of crystallization may be present. "Anhydrous" means essentially free of water including waters of crystallization. A number of peroxide complexes and their syntheses are described in U.S. Pat. No. 5,820,841.

It is preferred for the peroxide complex to be substantially insoluble in the compatible aprotic solvent and to be present during the reaction as a solid phase. Such peroxide complexes are easily removed after reaction by filtration or used in the form of a bed through which the acyl halide in compatible aprotic solvent is passed. Similarly, it is also preferred that the spent complex after reaction remain insoluble and in the solid phase.

Among the convenient inorganic peroxide complexes for the synthesis of diacyl peroxides according to this invention are percarbonate and perborate salts. These are most readily available as the sodium salts, which are used in the detergent industry. The other alkali metal salts of percarbonate or perborate, as for example, the potassium salts may also be used in accordance with this invention. Those skilled in the art will recognize that the alkaline earth percarbonates and perborates, as for example, the calcium salts, though less desirable because less readily available, would be expected to be useful according to the processes of this invention. For the purposes of this invention, although both the alkali metal and alkaline earth percarbonates and perborates have utility in the synthesis of diacyl peroxides, the alkali metal salts are preferable, and the sodium salts are more preferable. For convenience, the percarbonate salts and perborate salts will be referred to herein simply as percarbonate and perborate.

Sodium percarbonate, $Na_2CO_3 \cdot 1\frac{1}{2}H_2O_2$, is hydrolyzed by moisture, and for best results in the synthesis of diacyl peroxide according to this invention, the percarbonate should be kept dry. Sodium perborate, though represented as $NaBO_3 \cdot H_2O$ and sometimes called sodium perborate monohydrate, is reported to be $Na_2(B_2O_8H_4)$, and is therefore an anhydrous salt. Analogously, the so-called sodium perborate tetrahydrate is reported to be the trihydrate: $Na_2(B_2O_8H_4) \cdot 3H_2O$. The misnamed sodium perborate monohydrate is the preferred form to be used in the practice of this invention.

The organic peroxide complexes useful for carrying out this invention include those that may have some solubility in the compatible aprotic solvents, or at least be volatile enough to make separation from the compatible aprotic solvents difficult. The preferred organic complexes are those that are insoluble and whose residues are insoluble in the compatible aprotic solvents, and which are present during the synthesis as a solid phase. As such, they are easily separated from the diacyl peroxide solution. It is further desirable that the organic complexes be free of labile atoms or groups, or of bonds that can react with the reactants or products of the processes according to this invention, especially if such reactions degrade the organic molecule and such degradation products get into the reaction mixture.

Urea/hydrogen peroxide adduct (urea.$H_2O_2$) is a preferred organic peroxide complex. It is commercially available (Aldrich Chemical Co., Milwaukee Wis., USA). It is a solid and is essentially insoluble in the solvents designated herein and should small amounts be carried through filters or by other means into the diacyl peroxides solution, urea, not being active toward free-radical chain transfer, will have little effect on polymerization.

A significant advantage of the organic peroxide complexes is that they introduce no metal ions into reaction mixture and therefore give diacyl peroxide free of metal ions. In polymerization, such diacyl peroxide will introduce no metal ions into the polymer. Polymers, especially fluoropolymers, of low metal content, or free of metal ions, are needed for certain applications where high purity is required, such as the semiconductor industry.

An important characteristic of percarbonate, perborate, and urea/hydrogen peroxide adduct, and of the carbonate, borate, and urea remaining after their reaction, is their low solubility in the compatible aprotic solvents that are used in this invention and because they are in the solid phase under the reaction conditions. Because they are solids, they can be easily separated from reaction mixtures by filtration. For the same reason, percarbonate, perborate, and urea/hydrogen peroxide adduct may be used in beds for continuous synthesis of diacyl peroxides.

It is one of the advantages of the diacyl peroxide synthesis in accordance with this invention that any aprotic solvent or mixture thereof may be used that dissolves the organic acyl halide and the product diacyl peroxide, and is not otherwise incompatible with the product diacyl peroxide, or the reactants, the organic acyl halide and the percarbonate, or perborate, or urea/hydrogen peroxide adduct. Incompatible solvents include tertiary amines, because these can react with acyl halides and diacyl peroxides to form ammonium salts. Useful solvents include nonhalogenated solvents, and halocarbon solvents. In the class of nonhalogenated solvents are hydrocarbon solvents. These have utility in diacyl peroxide solutions that are used in polymerization of hydrocarbon monomers, but they are less useful for the polymerization of fluoromonomers because of the chain transfer activity characteristic of hydrocarbons in fluoromonomer polymerization. Halocarbon solvents, because of their low chain transfer activity, are therefore preferred because of their utility in both fluoromonomer and hydrocarbon monomer polymerizations.

Among the non-halogenated solvents, carbon dioxide in its liquid or supercritical states is preferred. It does not undergo chain transfer, is not reactive toward oxidizing agents such as diacyl peroxide, and being a gas at atmospheric pressure and room temperature, is easily removable from the products of polymerization. Surprisingly, it has been found that carbon dioxide, a Lewis acid, is an effective solvent for the production of diacyl peroxide by the reaction of acyl halides with peroxide complexes. This discovery provides a route to the direct synthesis in good yield of diacyl peroxides in carbon dioxide, minimizing the presence of water and eliminating any organic solvent such as would be inevitable in synthetic routes that would prepare the diacyl peroxide first in another solvent, subsequently replacing that solvent, by whatever means, with carbon dioxide. Carbon dioxide solutions of diacyl peroxide find particular utility in polymerizations conducted in carbon dioxide, because such initiator solution does not introduce a second solvent into the polymerization.

The halocarbon solvents include fluorocarbons, hydrofluorocarbons, hydrochlorofluorocarbons, chlorofluorocarbons, perhalocarbons, and perfluorocarbons. It is preferred that the in the hydrogen-containing halocarbon solvents, the hydrogens be non-labile, that is that they not be susceptible to significant chain-transfer in the presence of free radicals, especially during polymerization of fluoroolefins. Also useful are "halocarbon ethers", which are defined here as molecules containing at least one ether linkage in which the carbon atoms adjacent to the ether oxygen are completely halogenated, preferably completely fluorinated, or substituted with alkyl groups, preferably halogenated alkyl groups, and the monovalent atoms on the remaining carbon atoms being independently hydrogen, fluorine, or chlorine. Another class of useful solvents is perfluoroamines. In contrast to organic amines that are not fluorinated, the perfluoroamines have little or no basic character. Preferred compatible aprotic solvents are halocarbons, more preferably chlorofluorocarbons such as liquid $CF_2Cl-CFCl_2$ (CFC-113) and fluorocarbons such as liquid $CF_3CF_2CF_2OCF(CF_3)CF_2OCFHCF_3$ available as Fluoroether E2 from Lancaster Synthesis Inc., Windham, N.H., USA.

One of the unique aspects of this invention is that it permits direct production of diacyl peroxide in the solvent or solvents of choice without any trace of other solvent.

Because peroxide initiators are generally made, stored, and used in solution, it is desirable to choose a solvent that will not interfere with the polymerization reaction, as for example by undesired chain-transfer reactivity. It is better still if the initiator solvent is the same as the polymerization solvent. Then, with only a single solvent in the polymerization system, solvent removal and purification at the end of the reaction (for batch polymerizations) or in the recycle loop (for continuous polymerizations) is simplified.

The process according to this invention is substantially free of compounds that are oxidizable by the peroxide complex or by products of the reaction of organic acyl halide with peroxide complex, i.e., intermediate products or diacyl peroxide, under the conditions of the reaction. The identity of such compounds is known to those skilled in the art. Such materials include olefinic and acetylenic compounds, thiols, sulfides, disulfides, and other oxidizable sulfur compounds, alcohols, aldehydes, and ketones, and amines and other oxidizable nitrogen compounds. At low concentration, oxidizable compounds will decrease the yield of diacyl peroxide and may introduce undesirable impurities into the product that will affect subsequent polymerization. At higher concentrations, the presence of oxidizable compounds may make the reaction difficult to control and lead to excessive heat generation. By "substantially free" is meant that the oxidizable compounds are present in amounts that reduce the diacyl peroxide yield obtainable in the absence of the oxidizable compounds by no more than 50%, preferably by no more than 25%, more preferably by no more than 10%, and still more preferably by no more than 5%, and most preferably by no more than 1%.

As stated above, it is an advantage of this invention that diacyl peroxide is made without using aqueous alkaline peroxide solution, in contrast to the classical synthetic method. An aqueous phase is preferably not part of the process of this invention. Preferably, water per se is not added to the reaction. The presence of water will not completely prevent the production of diacyl peroxide but water will promote the formation of organic acid, (by hydrolysis of the organic acyl halide), and of peracid and/or organic acid (by hydrolysis of the diacyl peroxide). In addition, water that remains in the diacyl peroxide can cause corrosion in the polymerization equipment, particularly through hydrolysis of acid halides to produce hydrogen chloride and hydrogen fluoride. Water will also complicate the removal and purification of the polymerization solvent. These disadvantages caused by the presence of water become greater if enough water is present for a separate aqueous phase to form. Preferably, the amount of water is limited so as to prevent formation of a separate aqueous phase. For these reasons, care should be taken in the synthesis of diacyl peroxides according to this invention to have dry equipment and to keep the ingredients dry. If the reagents or the equipment is not completely dry, adding desiccants such as Drierite® (anhydrous calcium sulfate) to the reaction mixture may increase diacyl peroxide yield.

The temperature of the reaction is chosen to balance the interest in having a fast reaction, with the need to prevent loss of diacyl peroxide through thermal decomposition. Because diacyl peroxides vary in half-life (the time for one-half of the peroxide to be consumed; a function of temperature), reaction temperatures will vary, but useful temperatures are in the range of about −40° C. to about 40° C. For diacyl peroxides such as HFPO dimer peroxide, heptafluorobutyryl peroxide, isobutyryl peroxide, and bis [perfluoro(fluorosulfonyl)acetyl] peroxide, a temperature range of about −20° C. to about 20° C. is typical, about −10° C. to about 10° C. is preferred, and about −5° C. to about 5° C. is more preferred when sodium percarbonate or sodium perborate is used. When urea/hydrogen peroxide adduct is used to make these diacyl peroxides, about 0° C. to about 10° C. is the more preferred temperature. Diacyl peroxide loss to thermal decomposition is best minimized by keeping reaction time a fraction of the diacyl peroxide's half-life at reaction temperature. A reaction time no greater than one-quarter of the diacyl peroxide half-life at the reaction temperature is preferred.

Because residual acyl halide is an impurity in the product diacyl peroxide, and is furthermore a source of acid that can cause corrosion, it is desirable to conduct the synthesis so as to yield as much of the diacyl peroxide as possible. Yield is preferably at least about 25%, more preferably at least about 50%, more preferably still at least about 70%, and most preferably at least about 90%.

When diacyl peroxide is synthesized according to this invention in a batchwise manner, the reactant organic acyl halide is mixed in compatible aprotic solvent with peroxide complex. Surprisingly, it is found that the yield of diacyl peroxide increases as the mole ratio of peroxide in the peroxide complex to acyl halide increases. It is preferable that the mole ratio be at least about one to one. It is more preferable that the mole ratio be at least about two to one. It is most preferable that the mole ratio be at least about four to one. Because the peroxide content of the peroxide complex depends upon the nature of the complex, the weight of complex that contains a mole of peroxide or its equivalent will depend upon the composition of the complex being considered.

To prepare diacyl peroxide in a continuous reaction according to this invention, a feed stream comprised of organic acyl halide in compatible aprotic solvent is continuously contacted with a bed comprised of peroxide complex, in the absence of organic compounds susceptible to oxidation under the reaction conditions to form a product stream comprising diacyl peroxide in compatible aprotic solvent. The bed may be in the form of a column filled with peroxide complex and optionally an inert material. The purpose of the inert material would be to facilitate flow and temperature control. As stated above, the synthesis should be run so as to achieve high yield of the diacyl peroxide. The continuous method is preferred because it allows diacyl peroxide to be made as needed and consumed promptly. If desired, the diacyl peroxide in compatible aprotic solvent can be collected and advantageously used directly in that form. The continuous process ensures that fresh diacyl peroxide is always available and eliminates the need for diacyl peroxide storage, which generally requires low temperatures, and is therefore vulnerable to power outages and equipment failure. Furthermore, as with any oxidizing agent, it is sound practice to minimize the quantities of diacyl peroxide kept on hand. Both batch and continuous methods are demonstrated in the Examples.

EXAMPLES

Glossary

HFPO=Hexafluoropropylene oxide
HFPO Dimer Peroxide=$CF_3CF_2CF_2OCF(CF_3)(C=O)OO(C=O)(CF_3)CFOCF_2CF_2CF_3$
HFPO Dimer Acid Fluoride=$CF_3CF_2CF_2OCF(CF_3)(C=O)F$
DAF=HFPO Dimer Acid Fluoride
CFC-113=$CF_2Cl-CFCl_2$
Vertrel® XF=$CF_3CFHCHFCF_2CF_3$ (2,3-dihydroperfluoropentane) available from the DuPont Company, Wilmington, Del., USA
Fluoroether E2=$CF_3CF_2CF_2OCF(CF_3)CF_2OCFHCF_3$ (2H-Perfluoro-5-methyl-3,6-dioxanonane) available from Lancaster Synthesis Inc., Windham, N.H., USA Test Method Diacyl peroxides formed by this process are analyzed by peroxide titration using the following standard procedure. In a loosely stoppered Erlenmeyer flask, several grams of dry ice are added to 25 ml of glacial acetic acid, thereby flushing oxygen from the system. 5.0 ml of a solution of 30 g of potassium iodide in 70 ml of deoxygenated water is added, and then 5.0 ml of the peroxide solution to be analyzed is added. The mixture is stirred for 30 minutes to allow the peroxide to react with the iodide. 100 ml of deoxygenated water is added and the reaction mixture, having a deep iodine color, is titrated to light yellow with 0.1N sodium thiosulfate. Then 0.5 g of Thyodene® (Fisher Scientific Co.) iodometric indicator is added making the reaction mixture turn blue. Titration is continued with 0.1N sodium thiosulfate to a colorless endpoint. The molar peroxide concentration is 0.01 times the total number of ml of 0.1N sodium thiosulfate solution added to the reaction.

Example 1

HFPO Dimer Peroxide Synthesis in CFC-113 Using Sodium Percarbonate

A round-bottom flask is charged with 50 ml CFC-113 and 2.0 g of dry sodium percarbonate (13 mmoles of sodium percarbonate, or 19 mmoles of $H_2O_2$ equivalent). After chilling the contents of the flask to 0° C., 5.2 ml (25 mmole) of HPFO dimer acid fluoride (DAF) is added and the resulting slurry is stirred magnetically for 3 hours. The reaction mixture is filtered through a pad of Drierite® on glass wool, an operation assumed to remove any unreacted sodium percarbonate and any free $H_2O_2$. The filtrate is titrated and found to be 0.18 M in peroxide. Assuming a product volume of 55 ml, this is 9.9 mmole of peroxide or a 79% yield based on the starting organic acyl fluoride, DAF.

Example 2

HFPO Dimer Peroxide Synthesis in CFC-113 Using Sodium Perborate

A slurry of 4.9 g sodium perborate monohydrate (49 mmoles, Aldrich) in 75 ml of CFC-113 is stirred magnetically in a round-bottom flask under a positive pressure of nitrogen. The flask is immersed in a wet ice bath and, once its contents have chilled, 5.2 ml of HFPO dimer acid fluoride (25 mmoles) is added with stirring. The contents of the flask are stirred for 3 hours at 2° C. to 6° C. The reaction mixture is vacuum filtered, the filter pad rinsed with CFC-113, and the filtrate immediately washed through 25 g Drierite® with additional CFC-113. Passage through the Drierite® makes the solution noticeably hazy. This gives 69 ml of HFPO dimer peroxide solution that titrated 0.12 M in peroxide (66% yield). The next morning the product is washed three times with 50 ml of water and retitrated, coming out 0.13 M in peroxide (some of the CFC-113 may have evaporated in the washing process, increasing peroxide concentration).

Example 3

HFPO Dimer Peroxide Synthesis in CFC-113 Using Hydrated Sodium Perborate

A slurry of 7.7 g sodium perborate tetrahydrate (50 mmoles, Aldrich) in 75 ml of CFC-113 is stirred magnetically in a round-bottom flask under a positive pressure of nitrogen. The flask is immersed in a wet ice bath and, once its contents are chilled, 5.2 ml of HFPO dimer acid fluoride (25 mmoles) is added with stirring. The contents of the flask are stirred for 3 hours at 2° C. to 5° C. The reaction mixture was vacuum filtered, the filter pad rinsed with CFC-113, and the filtrate immediately washed through 25 g Drierite® with additional CFC-113. Passage through the Drierite® made the solution noticeably hazy. This gave 74 ml of HFPO dimer peroxide solution that titrates as 0.042 M in peroxide (25% yield). The next morning the product is washed three times with water and retitrated, coming out 0.046 M in peroxide (some of the CFC-113 may have evaporated in the washing process, increasing peroxide concentration).

The sodium perborate tetrahydrate, though effective in this synthesis, shows reduced yield of the dimer peroxide. This indicates that the presence of water is deleterious for the reaction. It is pointed out in the detailed description of the invention that sodium peroxide monohydrate is actually an anhydrous salt, and that sodium perborate tetrahydrate is in fact a trihydrate. The addition of a drying agent, such as Drierite®, might improve the yield by taking up the water introduced by the hydrated sodium perborate.

Examples 4–8

Influence of Ratio of Percarbonate to Acyl Halide

The experimental conditions of Example 1 are followed except that in place of CFC-113, the reaction solvent is Fluoroether E2, and concentrations of sodium percarbonate and DAF are varied to determine the effect of the ratio on product yield. Temperatures are maintained at 0° C. Results are summarized in Table 1. The 104% yield result may be due to evaporation of solvent in the course of analysis, or it may be experimental error.

TABLE 1

| | Mole Ratio | | | |
|---|---|---|---|---|
| Example | Percarbonate | DAF | Reaction Time | Yield |
| 4 | 1 | 1 | 3 hrs | 61% |
| 5 | 1.5 | 1 | 3 hrs | 79% |

TABLE 1-continued

| | Mole Ratio | | | |
|---------|-------------|-----|---------------|-------|
| Example | Percarbonate | DAF | Reaction Time | Yield |
| 6 | 2 | 1 | 3 hrs | 89% |
| 7 | 4 | 1 | 3 hrs | 104% |
| 8 | 1.5 | 1 | 0.5 hrs | 31% |

Examples 4 to 8 show that increasing the ratio of percarbonate to acyl halide increases yield. This is contrary to the prior art (McKillop and Sanderson, p. 6152) as well as to expectations based on the stoichiometry of the reaction. Equation (2) shows the desired reaction between the peroxide complex, represented simply as hydrogen peroxide, and acyl halide:

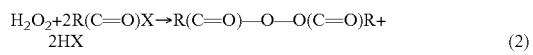
$$H_2O_2 + 2R(C=O)X \rightarrow R(C=O)-O-O(C=O)R + 2HX \qquad (2)$$

The competing, undesirable reaction is the formation of peracid, shown in Equation (3):

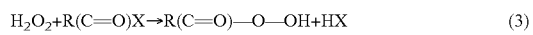
$$H_2O_2 + R(C=O)X \rightarrow R(C=O)-O-OH + HX \qquad (3)$$

Increasing the ratio of peroxide to acyl halide should increase the reaction of Equation (3), and decrease that of Equation (2). Surprisingly, the reverse is observed.

Example 9

Isobutyryl Peroxide Synthesis

A round-bottom flask is charged with 50 ml of CFC-113 and 2.0 g of sodium percarbonate (13 mmoles or 19 mmoles of $H_2O_2$ equivalent). After chilling the contents of the flask to 0° C., 2.60 ml of isobutyryl chloride (25 mmoles) is added and the resulting slurry is stirred magnetically for 223 minutes. The reaction mixture is filtered through a pad of Drierite® on glass wool, washing through with fresh CFC-113. The filtrate, now measuring 59 ml in volume, is found to be 0.083 M in peroxide, which is a 39% yield based on starting isobutyryl chloride. The peroxide solution is washed three times with ~60 ml of water. The washed solution is retitrated and found to be 0.050 M in peroxide. The water wash may have removed residual inorganic peroxide missed by the Drierite® filtration, but is more likely that some of the isobutyryl peroxide was destroyed by hydrolysis.

This example shows that the process of this invention can be used to prepare hydrocarbon acyl peroxides as well as fluorocarbon acyl peroxides.

Example 10

Heptafluorobutyryl Peroxide Synthesis

A round-bottom flask is charged with 50 ml of CFC-113 and 2.0 g of sodium percarbonate (13 mmoles or 19 mmoles of $H_2O_2$ equivalent). After chilling the contents of the flask to 0° C., 3.73 ml of heptafluorobutyryl chloride (25 mmoles) is added and the resulting slurry is stirred magnetically for 3.3 hours. The reaction mixture is filtered through a pad of Drierite® on glass wool, washing through with fresh CFC-113, an operation assumed to remove any unreacted percarbonate and any free $H_2O_2$. The filtrate, now measuring 45 ml in volume, is found to be 0.10 M in peroxide for a 37% yield based on starting heptafluorobutyryl chloride. In order to make sure that all of the sodium percarbonate and hydrogen peroxide has been removed by filtration through Drierite®, the peroxide solution is washed three times with 45–50 ml of water. On retitration, the solution is found to still be 0.10 M in peroxide.

Example 11

Bis[perfluoro(fluorosulfonyl)acetyl] Peroxide Synthesis

A round-bottom flask is charged with 50 ml of CFC-113 and 2.0 g of sodium percarbonate (13 mmoles or 19 mmoles of $H_2O_2$ equivalent). After chilling the contents of the flask to 0° C., 2.83 ml of $FSO_2CF_2(C=O)F$ (25 mmoles) is added and the resulting slurry is stirred magnetically for 3 hours. The reaction mixture is filtered through a pad of Drierite® on glass wool, washing through with fresh CFC-113, an operation assumed to remove any unreacted percarbonate and any free $H_2O_2$. The filtrate, now measuring 52 ml in volume, is found to be 0.10 M in peroxide for a 42% yield based on starting $FSO_2CF_2(C=O)F$.

This example shows that acyl halides with hydrolyzable functional groups can be converted by the method of this invention to diacyl peroxides, without affecting the hydrolyzable functional group.

Example 12

HFPO Dimer Peroxide Synthesis in CFC-113 Using Urea Hydrogen Peroxide Adduct

A round bottomed flask under a positive pressure of nitrogen gas is charged with 75 ml of CFC-113, 2.65 g of $Na_2CO_3$ (25 mmole), 2.35 g urea/hydrogen peroxide adduct (25 mmoles, $H_2NCONH_2.H_2O_2$), and 5.2 ml of HFPO dimer acid fluoride (25 mmole) with ice bath cooling. The reaction mixture is stirred for 3 hours at −7° C. to 2° C. (mostly at 1° C. to 2° C.), washed though a vacuum filter with CFC-113, and washed through 25 g of Drierite® in a chromatography column with CFC-113. This gives 97 ml of CFC-113 solution that titrates 0.046 M in peroxide (37% yield). After washing the CFC-113 solution three times with ice water, it still titrates 0.046M in peroxide.

Example 13

HFPO Dimer Peroxide Synthesis in Liquid Carbon Dioxide

A 300 ml stainless steel autoclave, equipped with a paddle stirrer and dip tube, is dried by heating to 100° C. for several hours under a dry nitrogen purge. Dry sodium percarbonate ($Na_2CO_3.1\frac{1}{2}H_2O_2$) (2 g (12.7 mmol)) is added and the autoclave is sealed, evacuated, and cooled to about −20° C.

Separately, a 1-liter stainless steel cylinder is charged with 5.2 ml (24.7 mmol) of HFPO dimer acid fluoride (DAF). The cylinder is cooled on dry ice and evacuated, and about 220 g of carbon dioxide is admitted. The cylinder is then connected to the autoclave using ⅛ inch (3.2 mm) diameter stainless steel tubing. The cylinder is inverted to transfer the entire contents of the cylinder to the autoclave. Prior vacuum of the autoclave and prior chilling of the autoclave promotes good transfer. About 199 g of the HFPO dimer acid fluoride/ liquid carbon dioxide mix is transferred from the stainless steel cylinder into the autoclave.

The contents of the autoclave are stirred at about 5000 rpm for four hours at 0° C. Temperature fluctuates mildly during this time from −2° C. to 0.5° C. The internal pressure in the autoclave varies from 477 psi (3.29 MPa) at −2° C. to 520 psi (3.59 MPa) at 0.5° C. After about four hours, the autoclave is chilled to −27° C. with the contents still stirring. Chilling to −27° C. reduces the internal pressure of the autoclave to 184 psi (1.27 MPa). A 1-liter pressure-resistant cylinder is evacuated and cooled in a liquid nitrogen bath. The cylinder is then connected to the dip tube outlet on the autoclave using an 18 inch (45 cm) length of ⅛ inch (3.2 mm) diameter stainless steel tubing. The contents of the autoclave are then vented into the stainless steel cylinder through the dip tube. At the end of the transfer, the pressure in the cylinder is 0.2 atm (20 kPa). A valve on the top of the cylinder is removed and 100 ml of Vertrel® XF is added so that the diacyl peroxide in the carbon dioxide can be transferred in the Vertrel® XF to facilitate measurement of reaction yield. The valve is replaced on the cylinder. The cylinder is removed from the liquid nitrogen bath. Contents of the cylinder are allowed to warm until rapid carbon dioxide evolution ceases. Evolution of carbon dioxide is judged by periodically opening and closing the cylinder valve and noting pressure changes.

Once carbon dioxide is no longer being rapidly evolved and frost on the sides of the cylinder shows the first signs of thawing (about 30–45 minutes), the valve is removed from the top of the cylinder. Contents of the cylinder, a hazy gray/blue fluid, are poured into a polyethylene bottle chilled on dry ice.

Opening the 300 ml autoclave at this point reveals residual white solid on the bottom and traces of white film on the walls of the autoclave. On visual inspection, the amount of solids left in the autoclave is observed to be approximately the same volume as the amount of sodium percarbonate added at the start.

The gray/blue fluid recovered from the reactor measures 85 ml in volume. Peroxide titration of 5.0 ml takes 5.95 ml of 0.1 N thiosulfate. This titration corresponds to a 41% yield of HFPO dimer peroxide.

The remaining gray/blue fluid, measuring 80 ml, is warmed from −78° C. to room temperature and washed three times in a separatory funnel with water. This water wash removes any unreacted sodium percarbonate and hydrogen peroxide that would titrate the same as the HFPO dimer peroxide. A 5 ml aliquot of the solution now takes 6.40 ml of 0.1 N thiosulfate in peroxide titration (the increase in peroxide concentration may reflect some evaporation of the Vertrel® XF solvent during the water wash).

Example 14

Continuous Synthesis of HFPO Dimer Peroxide in Liquid Carbon Dioxide

A 150 ml stainless steel cylinder is evacuated and charged with 7.90 g of perfluoro(2-methyl-3-oxa-hexanoyl) fluoride ($CF_3CF_2CF_2OCF(CF_3)COF$) ("DAF") and 50 g carbon dioxide. The cylinder, equipped with a pressure gauge is inverted and placed in a stand fixed to a balance. $\frac{1}{16}$ inch (1.6 mm) diameter stainless steel tubing is connected from the cylinder to the top of a stainless steel column about 0.56 cm in diameter and 10 cm in length. The column is packed with 10.0 g of sodium percarbonate. A plug of glass wool at the bottom of the column keeps the sodium percarbonate in the column. The column is immersed in a constant temperature bath at 0° C. A short length of $\frac{1}{16}$ inch (1.6 mm) stainless steel tubing runs from a valve at bottom of the column, through a rubber septum, and into a cold trap that is immersed in a dry-ice/acetone slurry and vented to the atmosphere. The trap contains about 50 g Vertrel® XF.

The cylinder valve is opened allowing the liquid DAF/$CO_2$ mixture to fill the column. The valve between the bottom of the column and the cold trap is then opened slightly to permit a controlled flow of material through the column at a rate of 0.154 g/min. The void volume in the column is 6.0 ml. The void volume divided by the flow rate of material through the column is taken as the contact time. The contact time is 39 minutes. The non-volatile effluent from the column is taken up in the cold trap to form a solution in Vertrel® XF. The low temperature of the trap preserves the diacyl peroxide formed, and the solvent provides a convenient medium for subsequent product analysis. Most of the $CO_2$ is vented spontaneously to the atmosphere from the trap. At the conclusion of the experiment, the cold trap is warmed to 0° C. in ice water and vigorously agitated until the weight of the trap remains constant to remove any remaining $CO_2$. Peroxide titration of aliquots of solution from the cold trap shows that 4.81 g of peroxide is formed. Its identity is confirmed from absorption at 1858 $cm^{-1}$ and 1829 $cm^{-1}$ in its infrared spectrum arising from carbonyl groups in the diacyl peroxide. The amount of DAF remaining in the collected product is 2.19 g as determined from the intensity of the infrared absorption at 1881 $cm^{-1}$ arising from the acid fluoride carbonyl group. From these data yield of peroxide is calculated to be 68.7%.

Example 15

Continuous Synthesis of HFPO Dimer Peroxide in Liquid Carbon Dioxide

The procedure and equipment are as described in Example 14 except the 4.74 g DAF is charged in the cylinder, the feed rate is 0.129 g/min, and the contact time is 46 minutes. Product collected is 4.02 g, and 0.67 g remains on the column. The product consists of 2.94 g peroxide and 1.41 g of recovered DAF. Yield is 67.6%.

Example 16

Continuous Synthesis of HFPO Dimer Peroxide in Liquid Carbon Dioxide

The procedure and equipment are as described in Example 14. The feed rate is 0.0697 g/min, and the contact time is 86 minutes. Product collected is 7.01 g and 1.53 g remain on the column. The product consists of 6.23 g peroxide and 0.43 g of recovered DAF. Yield is 93.56%.

Example 17

Continuous Synthesis of HFPO Dimer Peroxide in Liquid Carbon Dioxide

The procedure and equipment are as described in Example 14 except the temperature of the bath around the column is maintained at 10° C., the feed rate is 0.165 g/min, and the contact time is 32 minutes. Product collected is 5.87 g, and 1.89 g remains on the column. The product consists of 5.36 g peroxide and 0.43 g of recovered DAF. Yield is 91.3%.

Example 18

Continuous Synthesis of HFPO Dimer Peroxide in Liquid Carbon Dioxide

The procedure and equipment are as described in Example 14 except the temperature of the bath around the column is maintained at 15° C., the feed rate is 0.242 g/min, and the contact time is 20 minutes. Product collected is 5.92 g, and 1.69 g remains on the column. The product consists of 5.13 g peroxide and 1.02 g of recovered DAF. Yield is 83.4%.

Summary of Examples 14 to 18

Table 2 summarizes the results of the examples of the continuous synthesis of diacyl peroxide. Yields are increased with longer contact time or with higher reaction temperature.

TABLE 2

| Example | Contact Time (min) | Temperature (° C.) | Yield (%) |
|---|---|---|---|
| 14 | 39 | 0 | 68.7 |
| 15 | 46 | 0 | 67.6 |
| 16 | 86 | 0 | 93.6 |
| 17 | 32 | 10 | 91.3 |
| 18 | 20 | 15 | 83.4 |

Example 19

HFPO Dimer Peroxide Synthesis in Carbon Dioxide Using Urea Hydrogen Peroxide Adduct A jacketed autoclave of 125 ml volume is heated to 60° C. and purged with nitrogen for several hours. The autoclave is then cooled to room temperature and 3.0 g (30.9 mmoles $H_2O_2$ equivalent) urea/hydrogen peroxide adduct (Aldrich Chemical Co.), containing 35.0% $H_2O_2$ by peroxide titration, is added under a stream of nitrogen. The autoclave is closed, evacuated, and cooled to −20° C. A cylinder, into which 16.0 g of HFPO dimer acid fluoride (48.2 mmoles) and 60 g of carbon dioxide had been charged, is connected to the autoclave and the contents of the cylinder are transferred into the autoclave. The temperature of the autoclave is then raised to 0° C. while its contents are agitated for 6 hrs. The bottom port of the autoclave is fitted with a sintered metal filter containing 15 micrometer pores to retain urea and unused urea/hydrogen peroxide adduct. The contents of the autoclave are vented into an accurately weighed nitrogen flushed cold trap immersed in a dry ice/acetone bath. The trap contained about 50 g of Vertrel® XF. The solvent is used to absorb the reaction mixture as most of the carbon dioxide is vented to the atmosphere. This also provided a convenient medium for infrared analysis of the reaction mixture at room temperature and atmospheric pressure.

The cold trap and its contents are warmed to 0° C. in an ice bath with shaking to expel remaining carbon dioxide from the Vertrel® XF solution. The trap is dried and weighed and used to determine the weight of the product solution obtained. A portion of the solution is then placed in a liquid infrared cell and its spectrum measured. A reference spectrum of Vertrel® XF previously obtained in the same liquid cell is subtracted from that of the product mixture and intensities of bands occurring at 1858 $cm^{-1}$ and 1829 $cm^{-1}$ for the HFPO dimer peroxide, 1880 $cm^{-1}$ for the HFPO dimer acid fluoride and 1774 $cm^{-1}$ for the HFPO dimer acid are determined. Calibration curves determined from solutions of known concentration are used to calculate the amounts of each compound from the intensity of the appropriate infrared band in the spectrum of the product mixture. We found 60.6% HFPO dimer peroxide, 36.5% HFPO dimer acid fluoride and 3.0% HFPO dimer acid in the product mixture weighing 13.35 g.

Example 20

HFPO Dimer Peroxide Synthesis in Carbon Dioxide Using Urea Hydrogen Peroxide Adduct The procedure given in Example 19 is used except the temperature of the autoclave is raised to 5° C. We found 83.0% HFPO dimer peroxide, 12.5% HFPO dimer acid fluoride and 4.5% HFPO dimer acid in the product mixture weighing 15.32 g.

Example 21

HFPO Dimer Peroxide Synthesis in Carbon Dioxide Using Urea Hydrogen Peroxide Adduct The procedure given in Example 19 is used except the temperature of the autoclave is raised to 10° C. and agitation is continued for 3 hrs. We found 76.1% HFPO dimer peroxide, 15.5% HFPO dimer acid fluoride and 8.4% HFPO dimer acid in the product mixture weighing 12.36 g.

Example 22

HFPO Dimer Peroxide Synthesis in Carbon Dioxide Using Urea Hydrogen Peroxide Adduct The procedure given in Example 19 is used except 2.9 g of urea is added to the autoclave along with the urea/hydrogen peroxide adduct to serve as a mild base to absorb HF generated during the reaction. The temperature of the autoclave is also raised to 5° C. We found 81.4% HFPO dimer peroxide, 15.4% HFPO dimer acid fluoride and 3.2% HFPO dimer acid in the product mixture weighing 7.11 g.

Example 23

HFPO Dimer Peroxide Synthesis in Carbon Dioxide Using Urea Hydrogen Peroxide Adduct The procedure given in Example 19 is used except the amount of urea/hydrogen peroxide adduct charged to the autoclave is 5.0 g (51.5 mmoles $H_2O_2$ equivalent) and the temperature of the autoclave is raised to 5° C. We found 87.8% HFPO dimer peroxide, 6.4% HFPO dimer acid fluoride and 5.8% HFPO dimer acid in the product mixture weighing 16.39 g.

Summary of Examples 19 to 23

Table 3 summarizes the results of the examples of the synthesis of diacyl peroxide using urea/hydrogen peroxide adduct. Yields are increased with longer contact time or with higher reaction temperature. Increasing the ratio of urea/hydrogen peroxide adduct to acyl fluoride (DAF) increases yield. Added urea has little or no effect.

TABLE 3

| Example | Contact Time (hour) | Temperature (° C.) | DAF:H$_2$O$_2$ (mmoles) | Yield (%) |
|---|---|---|---|---|
| 20 | 6 | 0 | 48.2:30.9 | 47.2 |
| 21 | 6 | 5 | 48.2:30.9 | 83.0 |
| 22 | 3 | 10 | 48.2:30.9 | 76.1 |
| 23* | 6 | 5 | 48.2:30.9 | 81.4 |
| 24 | 6 | 5 | 48.2:51.5 | 87.8 |

*Urea added as mild base.

What is claimed is:

1. A process for the polymerization of olefin monomer comprising:

contacting organic acyl halide and peroxide complex in aprotic solvent to produce a diacyl peroxide solution comprising diacyl peroxide dissolved in said aprotic solvent, said aprotic solvent being compatible with the diacyl peroxide, organic acyl halide and peroxide complex and being substantially free of compounds oxidizable by the peroxide complex or by products of the reaction of organic acid halide with peroxide complex, said aprotic solvent being chosen to not interfere with said polymerization of said olefin monomer;

limiting the amount of water present during said contacting so as to prevent formation of an aqueous phase;

collecting said diacyl peroxide solution; and initiating polymerization of said olefin monomer with said diacyl peroxide contained in said diacyl peroxide solution, said diacyl peroxide solution being used directly in said polymerization of said olefin monomer.

2. A process for the polymerization of olefin monomer comprising:

contacting organic acyl halide and peroxide complex in aprotic solvent to produce a diacyl peroxide solution comprising diacyl peroxide dissolved in said aprotic solvent, said aprotic solvent being compatible with the diacyl peroxide, organic acyl halide and peroxide complex and being substantially free of compounds oxidizable by the peroxide complex or by products of the reaction of organic acid halide with peroxide complex, said aprotic solvent being chosen to not interfere with said polymerization of said olefin monomer;

limiting the amount of water present during said contacting so as to prevent formation of an aqueous phase;

collecting said diacyl peroxide solution; and initiating polymerization of said olefin monomer with said diacyl peroxide contained in said diacyl peroxide solution, said contacting being carried out at a reaction temperature selected so that the reaction time is no greater than one-quarter of the diacyl peroxide half-life at the reaction temperature.

3. A process for the polymerization of olefin monomer comprising:

contacting organic acyl halide and peroxide complex in aprotic solvent to produce a diacyl peroxide solution comprising diacyl peroxide dissolved in said aprotic solvent, said aprotic solvent being compatible with the diacyl peroxide, organic acyl halide and peroxide complex and being substantially free of compounds oxidizable by the peroxide complex or by products of the reaction of organic acid halide with peroxide complex, said aprotic solvent being chosen to not interfere with said polymerization of said olefin monomer;

limiting the amount of water present during said contacting so as to prevent formation of an aqueous phase;

collecting said diacyl peroxide solution; and initiating polymerization of said olefin monomer with said diacyl peroxide contained in said diacyl peroxide solution, the organic acyl halide being selected from the group consisting of fluoroorganic acyl halides.

4. A process for the polymerization of olefin monomer comprising:

contacting organic acyl halide and peroxide complex in aprotic solvent to produce a diacyl peroxide solution comprising diacyl peroxide dissolved in said aprotic solvent, said aprotic solvent being compatible with the diacyl peroxide, organic acyl halide and peroxide complex and being substantially free of compounds oxidizable by the peroxide complex or by products of the reaction of organic acid halide with peroxide complex, said aprotic solvent being chosen to not interfere with said polymerization of said olefin monomer;

limiting the amount of water present during said contacting so as to prevent formation of an aqueous phase;

collecting said diacyl peroxide solution; and initiating polymerization of said olefin monomer with said diacyl peroxide contained in said diacyl peroxide solution, the organic acyl halide being selected from the group consisting of perfluoroorganic acyl halides.

5. A process for the polymerization of olefin monomer comprising:

contacting organic acyl halide and peroxide complex in aprotic solvent to produce a diacyl peroxide solution comprising diacyl peroxide dissolved in said aprotic solvent, said aprotic solvent being compatible with the diacyl peroxide, organic acyl halide and peroxide complex and being substantially free of compounds oxidizable by the peroxide complex or by products of the reaction of organic acid halide with peroxide complex, said aprotic solvent being chosen to not interfere with said polymerization of said olefin monomer;

limiting the amount of water present during said contacting so as to prevent formation of an aqueous phase;

collecting said diacyl peroxide solution; and initiating polymerization of said olefin monomer with said diacyl peroxide contained in said diacyl peroxide solution, the organic acyl halide being isobutyryl halide.

6. A process for the polymerization of olefin monomer comprising:

contacting organic acyl halide and peroxide complex in aprotic solvent to produce a diacyl peroxide solution comprising diacyl peroxide dissolved in said aprotic solvent, said aprotic solvent being compatible with the diacyl peroxide, organic acyl halide and peroxide complex and being substantially free of compounds oxidizable by the peroxide complex or by products of the reaction of organic acid halide with peroxide complex, said aprotic solvent being chosen to not interfere with said polymerization of said olefin monomer;

limiting the amount of water present during said contacting so as to prevent formation of an aqueous phase;

collecting said diacyl peroxide solution; and initiating polymerization of said olefin monomer with said diacyl peroxide contained in said diacyl peroxide solution, the compatible aprotic solvent being selected from the group consisting of a halocarbon, chlorofluorocarbon hydrochlorofluorocarbon, hydrochlorocarbon, hydrofluorocarbon, perfluorocarbon, halocarbon ether and mixtures thereof.

7. A process for the polymerization of olefin monomer comprising:
  contacting organic acyl halide and peroxide complex in aprotic solvent to produce a diacyl peroxide solution comprising diacyl peroxide dissolved in said aprotic solvent, said aprotic solvent being compatible with the diacyl peroxide, organic acyl halide and peroxide complex and being substantially free of compounds oxidizable by the peroxide complex or by products of the reaction of organic acid halide with peroxide complex, said aprotic solvent being chosen to not interfere with said polymerization of said olefin monomer;
  limiting the amount of water present during said contacting so as to prevent formation of an aqueous phase;
  collecting said diacyl peroxide solution; and
  initiating polymerization of said olefin monomer with said diacyl peroxide contained in said diacyl peroxide solution, the compatible aprotic solvent being liquid or supercritical carbon dioxide.

8. A process for the polymerization of olefin monomer comprising:
  contacting organic acyl halide and peroxide complex in aprotic solvent to produce a diacyl peroxide solution comprising diacyl peroxide dissolved in said aprotic solvent, said aprotic solvent being compatible with the diacyl peroxide, organic acyl halide and peroxide complex and being substantially free of compounds oxidizable by the peroxide complex or by products of the reaction of organic acid halide with peroxide complex, said aprotic solvent being chosen to not interfere with said polymerization of said olefin monomer;
  limiting the amount of water present during said contacting so as to prevent formation of an aqueous phase;
  collecting said diacyl peroxide solution; and
  initiating polymerization of said olefin monomer with said diacyl peroxide contained in said diacyl peroxide solution, said polymerization being carried out in a polymerization solvent and said polymerization solvent being the same as said aprotic solvent.

9. A process for the polymerization of olefin monomer comprising:
  contacting organic acyl halide and peroxide complex in aprotic solvent to produce a diacyl peroxide solution comprising diacyl peroxide dissolved in said aprotic solvent, said aprotic solvent being compatible with the diacyl peroxide, organic acyl halide and peroxide complex and being substantially free of compounds oxidizable by the peroxide complex or by products of the reaction of organic acid halide with peroxide complex, said aprotic solvent being chosen to not interfere with said polymerization of said olefin monomer;
  limiting the amount of water present during said contacting so as to prevent formation of an aqueous phase;
  collecting said diacyl peroxide solution; and
  initiating polymerization of said olefin monomer with said diacyl peroxide contained in said diacyl peroxide solution, said polymerization producing a fluoropolymer and said monomer being selected from the group consisting of tetrafluoroethylene, hexafluoropropylene, perfluoro(alkyl vinyl ethers), chlorotrifluoroethylene, vinylidene fluoride, vinyl fluoride, ethylene and perfluoroalkylethylene.

10. A process for the polymerization of olefin monomer comprising:
  continuously contacting a feed stream comprised of organic acyl halide in aprotic solvent with a bed comprised of peroxide complex to form a product stream comprised of diacyl peroxide dissolved in said aprotic solvent, said aprotic solvent being compatible with the diacyl peroxide, organic acyl halide and peroxide complex and being substantially free of compounds oxidizable by peroxide complex or by products of the reaction of organic acid halide with peroxide complex, said aprotic solvent being chosen to not interfere with said polymerization of said olefin monomer;
  limiting the amount of water present during said contacting so as to prevent formation of an aqueous phase;
  collecting said product stream;
  initiating polymerization of said olefin monomer with said diacyl peroxide contained in said product stream.

11. The process of claim 10 wherein said diacyl peroxide solution is used directly for initiating said polymerization of said olefin monomer.

12. The process of claim 10 wherein said polymerization is carried out in a polymerization solvent and said polymerization solvent is the same as said aprotic solvent.

13. The process of claim 10 wherein said polymerization produces a fluoropolymer and said monomer is selected from the group consisting of tetrafluoroethylene, hexafluoroproplyene, perfluoro(alkyl vinyl ethers), chlorotrifluoroethylene, vinylidene fluoride, vinyl fluoride, ethylene and perfluoroalkylethylene.

* * * * *